United States Patent
Myrman et al.

(10) Patent No.: US 6,651,341 B1
(45) Date of Patent: Nov. 25, 2003

(54) FOIL CUTTER

(75) Inventors: Mattias Myrman, Stockholm (SE); Herbert Grässl, Schwandorf (DE)

(73) Assignee: Microdrug AG, Hergiswil (CH)

( * ) Notice: Subject to any disclaimer, the term of this patent is extended or adjusted under 35 U.S.C. 154(b) by 52 days.

(21) Appl. No.: 09/686,086

(22) Filed: Oct. 12, 2000

(30) Foreign Application Priority Data

Sep. 25, 2000 (SE) .............................................. 0003410

(51) Int. Cl.$^7$ .............................. B65D 83/06; B67B 7/00
(52) U.S. Cl. .......................... 30/2; 128/203.15; 30/346
(58) Field of Search .............................. 30/278, 280, 1, 30/1.5, 2, 346; 222/80, 81, 82, 83, 83.5, 636; 128/203.15, 203.12, 203.21, 203.23; 604/58

(56) References Cited

U.S. PATENT DOCUMENTS

| | | | | |
|---|---|---|---|---|
| 2,549,303 A | * | 4/1951 | Friden | 128/203.15 |
| 4,105,027 A | * | 8/1978 | Lundquist | 128/203.15 |
| 4,995,385 A | * | 2/1991 | Valentini et al. | 128/203.15 |
| 5,533,502 A | * | 7/1996 | Piper | 128/203.16 |
| 5,622,166 A | * | 4/1997 | Eisele et al. | 128/203.15 |
| 5,660,169 A | * | 8/1997 | Kallstrand et al. | 128/203.15 |
| 5,669,378 A | * | 9/1997 | Pera et al. | 128/203.15 |
| 5,785,049 A | * | 7/1998 | Smith et al. | 128/203.15 |
| 5,881,719 A | * | 3/1999 | Gottenauer et al. | 128/203.15 |
| 6,065,472 A | * | 5/2000 | Anderson et al. | 128/203.15 |
| 6,116,238 A | * | 9/2000 | Jackson et al. | 128/203.15 |
| 6,209,538 B1 | * | 4/2001 | Casper et al. | 128/203.15 |
| 6,273,086 B1 | * | 8/2001 | Ohki et al. | 128/203.15 |

* cited by examiner

Primary Examiner—Boyer Ashley
Assistant Examiner—Thomas J Druan, Jr.
(74) Attorney, Agent, or Firm—Young & Thompson

(57) ABSTRACT

A foil-cutting device is disclosed for opening a foil protecting a dose of medical power carried by a dosing cassette or the like for an inhaler device. The dosing cassette will in a typical embodiment carry a number of prepared doses (31), which for protection of the medical powder are covered by a metallic or plastic foil (24). The foil-cutter device of the present invention provides a tool (11) for accessing a selected sealed dose of medical powder of the cassette during an inhalation process using a dry powder inhaler (DPI). When a user inhales through the DPI the foil-cutter opens the foil (24) for access to a pre-metered powder dose (31). The foil-cutter arrangement ensures that no access is permitted to the pre-metered dose during any other circumstances. Particularly the present invention is adapted to be applied in an inventive continuous inhaler prolonging the release of a powder dose during the inhalation of the medical powder.

5 Claims, 4 Drawing Sheets

FOIL CUTTER

TECHNICAL FIELD

The present invention relates to dry powder inhalers and more exactly to a foil cutter device for accessing a sealed dose onto a dosing member carrying one or several pre-metered powder doses for a dry powder inhaler.

BACKGROUND

Today supply and distribution of medical powders take place in many different ways. Within health care more and more is focussed on the possibility to dose and distribute powder directly to the lungs of a user by means of an inhaler to obtain an efficient, fast, and user friendly administration of the specific medical substance.

Inhalers have been developed from being very simple to the up-to-date relatively complicated devices. For the up-to-date inhalers some form of dosing process is almost entirely used for preparing the dose to be inhaled. Most often the dosing of the amount to be inhaled takes place industrially in advance in a dose package containing of the order 10–50 doses. The inhaler then is loaded with this dose package as the source of each dose. Other inhalers have a magazine from which the powder is dosed by some device for distribution to the inspiration air. In both cases the powder will generally be strongly agglomerated and therefore must be dispersed.

When it comes to a dry powder inhaler (DPI) one aspect that is of great importance is to keep the medical substance free from air humidity, dirt, or any other kind of pollution. In order to achieve this, the dose of powder needs to be kept in a sealed volume during storage and preferably, for as long as possible until the dose on a carrier element is to be inhaled. The material, used for sealing the dose may be for instance aluminum or some polymer foil. Such a foil should prevent all kind of leakage from the surrounding environment, both when it comes to penetration of the film as such, as well as a leakage between the foil and the edge walls of the carrier element to which the foil is fixed, e.g. by a welding or gluing process.

Therefore there is a demand for a device, which will prepare the dosing member for an immediate access to its pre-metered dose of the medical powder at the proper time in connection to an inhalation process for releasing a certain dose of the medical powder dispensed by the DPI.

SUMMARY

A dosing cassette or the like will in a typical embodiment carry a number of prepared doses, which for protection of the medical powder are covered by a metallic or plastic foil. The foil-cutter device of the present invention provides a tool for accessing a sealed dose of medical powder of the cassette, which is placed into a dry powder inhaler (DPI). When a user inhales through the DPI the foil-cutter will open the foil for access to a pre-metered powder dose. The foil-cutter arrangement ensures that no access is permitted to the pre-metered dose during any other circumstances. Particularly the present invention is adapted to be applied in an inventive continuous inhaler prolonging the release of a powder dose during an inhalation.

DESCRIPTION OF THE DRAWINGS

The invention will be described in the form of a preferred and illustrative embodiment and by means of the attached drawings, wherein like reference numbers indicate like or corresponding elements and wherein.

DESCRIPTION OF AN ILLUSTRATIVE EMBODIMENT

Figure 1:
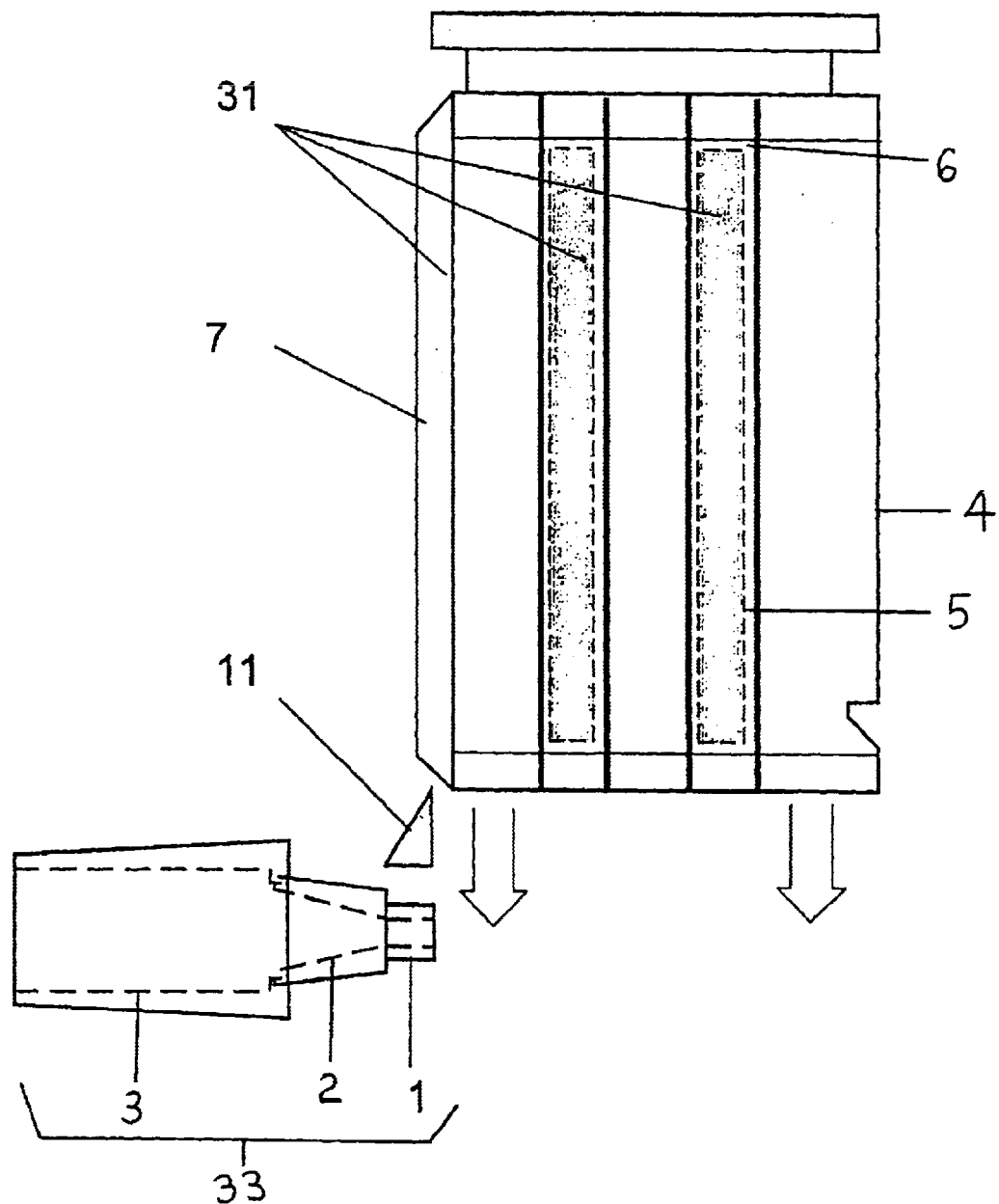
FIG. 1 illustrates in a side-view the mouthpiece suction tube, the cutter, and the cassette member with its pre-metered doses.

FIG. 1 an illustrative embodiment of the present invention is presented. A cassette 4 serves as a carrier of one or several doses of a medical drug to be administered in the form of a fine powder, which is to be inhaled by a user by means of a dry powder inhaler also referred to as a DPI (not shown). Each dose is placed on a separate dose bed 6 in dose carrying recesses 7 of the cassette 4. Each dose then has been individually sealed by a suitable foil strip 24.

Figure 2:
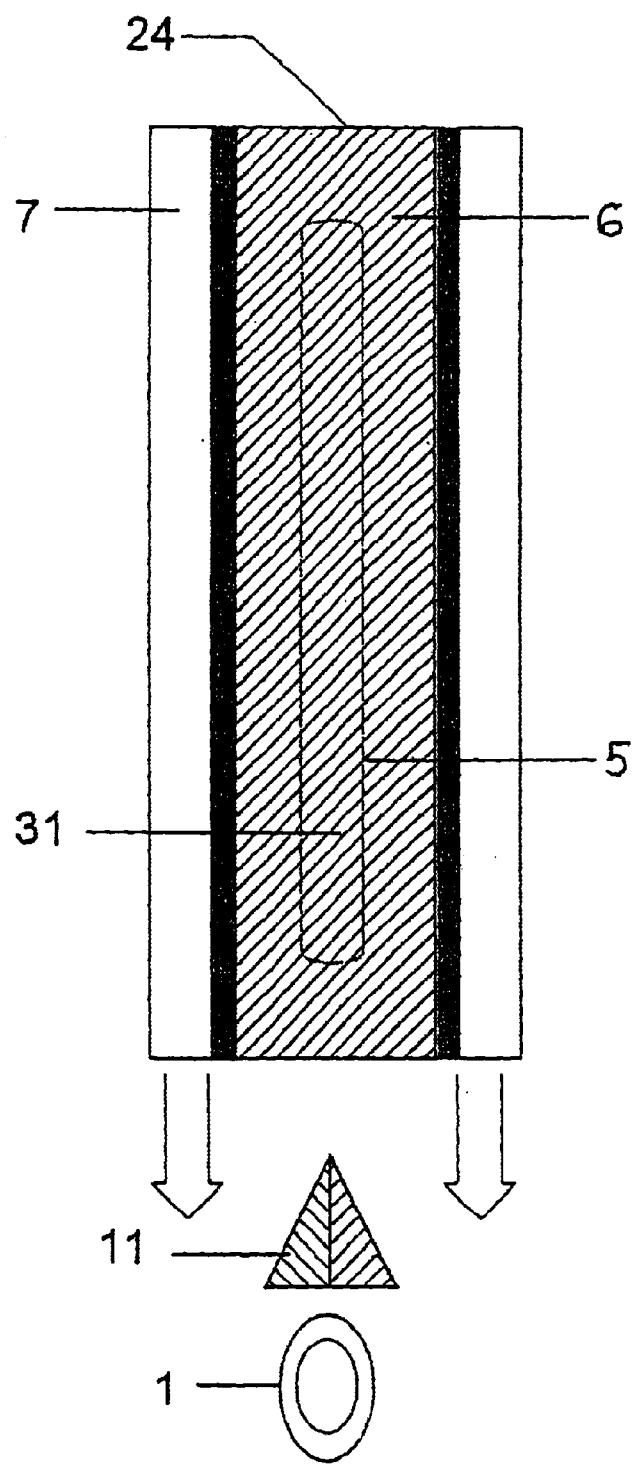
FIG. 2 illustrates in a top-view the mouthpiece, the cutter in an initial position at the cassette member with a foil enclosed pre-metered dose.

This powder dose has been pre-metered and applied to the cassette 4 in the form of a strip or a series of spots of powder on the dose bed 6, which is also illustrated in FIG. 2 showing the arrangement in a top view. The foil 24 covers the entire strip of powder such that there is formed a closed and sealed volume for each dose of powder 31, as indicated in FIG. 1. When a cassette to be used is inserted into the DPI, it is in advance prepared in this way.

Figure 3:
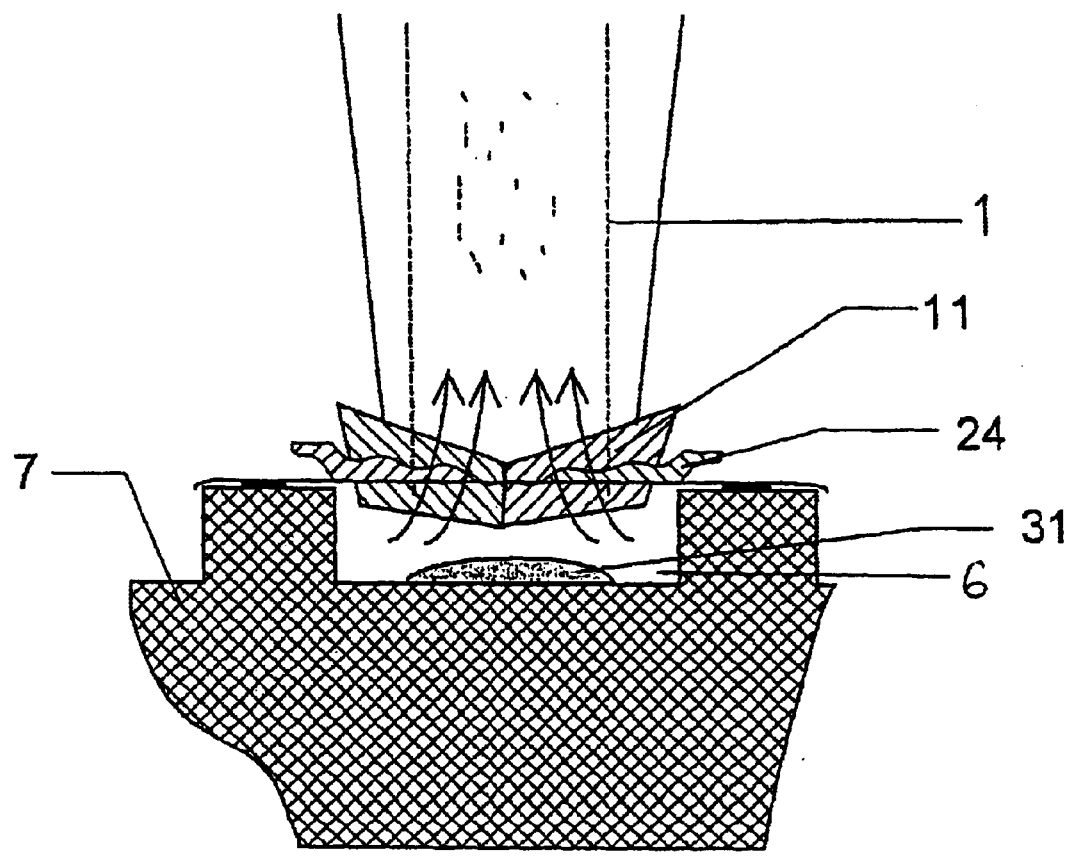
FIG. 3 illustrates a cross section of the cassette and the cutter cutting the foil for accessing the powder dose.

When an inhalation is performed the cassette 4, at the start of the inhalation, is released from its ready-to-go state by a catch mechanism. The cassette will then be propelled forward in an appropriate motion, for instance by a spring (not shown). The cassette 4 with the dose to be administered moves towards the foil cutter 11 and the nozzle 1 of the suction tube 33, comprising besides the nozzle 1 a diffuser 2 and a porous tube 3, all of which fitted to the mouthpiece. At the point where the sharp edge of the cutter comes in contact with the foil 24, which seals the dose 31 in the cassette dose bed 6, the foil is cut open, as indicated in FIG. 3. It should be noted that the foil-cutter is not allowed to make contact with the powder on the dose bed 6, but should only open the foil so that the nozzle 1 can get access to the powder without restrictions.

Figure 4:
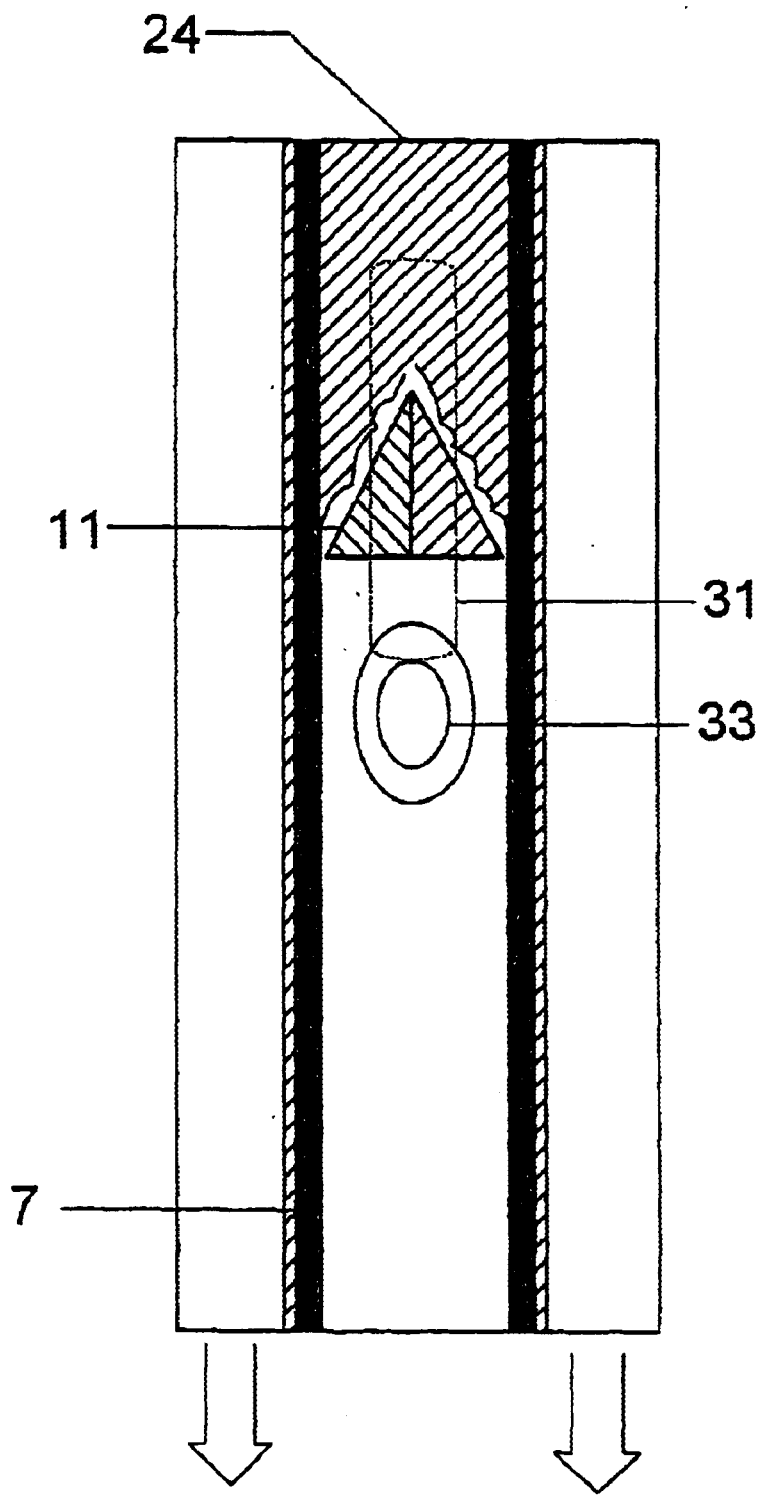
FIG. 4 illustrates the cassette with its pre-metered doses in motion, whereby the cutter exposes the powder dose to the suction tube nozzle sweeping over the dose bed during an inhalation.

During the continuous motion of the cassette 4 indicated in FIG. 3, the cutter 11 serves two functions; one is to cut the foil 24 open, a continuous action during the cassette motion, and the other is to fold the foil out of the way so it does not interfere with the nozzle 1 during the inhalation process. As the dose strip 5 is continuously transported by the cassette 4 under the nozzle 1 the powder is withdrawn from the dose bed 6 by the flow of air into the nozzle 1 resulting from the inhalation as is further indicated in FIGS. 3 and 4.

The powder is dispersed in the air as it goes up the diffuser 2 and porous tube 3 of the suction tube 33 of the mouthpiece and the speed of the air is suitably reduced to make the delivery of the dose to the upper or deep lungs with as little retention as possible in the mouthpiece parts or the airways of the user. The mouthpiece suction tube 33 is placed just behind the foil cutter 11.

It will be understood by those skilled in the art that various modifications and changes may be made to the present invention without departure from the scope thereof, which is defined by the appended claims.

What is claimed is:

1. Arrangement in a dry powder inhaler for cutting open a foil which protects a selected dose of medical powder carried by a dosing member, comprising a foil-cutter element having the form of a triangular wedge with a sharp point in front thereby forming a plough positioned in front of a nozzle of a mouthpiece suction tube;

a dosing member provided with prepared beds of powder covered by a protective foil;

wherein upon an inhalation process said dosing member is propelled towards said foil-cutter element and said protective foil is cut open laterally and folded upwardly and outwardly in relation to an underlying bed of powder by relative movement and contact between the foil-cutter element and the protective foil to make said nozzle access a selected bed of powder, the powder content of the selected bed of powder then being sucked into the inhalation air and transported into the lungs of the user during a prolonged time of the inhalation process.

2. The arrangement according to claim 1, wherein said foil-cutter element and said nozzle are adjacent to each other.

3. The arrangement according to claim 1, wherein said foil-cutter element forms a triangular wedge having a bottom side positioned at a height relative to said dosing member not to touch said bed of powder but only opening said foil for a free access of said nozzle to said bed of powder during the dosing member motion.

4. The arrangement according to claim 1, wherein said foil-cutter element and a selected bed of powder are propelled in relation to each other in two parallel planes, when the inhalation process occurs such that said foil-cutter element accesses the foil in order to cut and slit the foil open for access of said nozzle, without touching any of a powder making up a selected dose.

5. The arrangement of claim 1, wherein each prepared bed of powder has a longitudinal axis; said foil-cutter element comprises first and second sides that meet to form a knife edge; and whereby relative motion of the foil-cutter element and the dosing member along said longitudinal axis causes the sharp point of the foil-cutter element to penetrate said protective foil and the knife edge of the foil-cutter element to cut said protective foil along the length of the underlying prepared bed of powder.

* * * * *